US010500254B2

(12) United States Patent
Deykin

(10) Patent No.: US 10,500,254 B2
(45) Date of Patent: *Dec. 10, 2019

(54) METHOD FOR REDUCING FLU-LIKE SYMPTOMS ASSOCIATED WITH INTRAMUSCULAR ADMINISTRATION OF INTERFERON USING A FAST TITRATION ESCALATING DOSING REGIMEN

(71) Applicant: Biogen MA Inc., Cambridge, MA (US)

(72) Inventor: Aaron Deykin, Needham, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/695,587

(22) Filed: Sep. 5, 2017

(65) Prior Publication Data

US 2017/0360890 A1 Dec. 21, 2017

Related U.S. Application Data

(60) Continuation of application No. 14/936,228, filed on Nov. 9, 2015, now abandoned, which is a division of application No. 13/421,197, filed on Mar. 15, 2012, now Pat. No. 9,198,955.

(60) Provisional application No. 61/452,807, filed on Mar. 15, 2011, provisional application No. 61/476,930, filed on Apr. 19, 2011.

(51) Int. Cl.
*A61K 38/21* (2006.01)
*A61K 9/00* (2006.01)
*C07K 14/565* (2006.01)

(52) U.S. Cl.
CPC ............ *A61K 38/21* (2013.01); *A61K 9/0019* (2013.01); *A61K 38/215* (2013.01); *C07K 14/565* (2013.01); *A61K 2300/00* (2013.01)

(58) Field of Classification Search
CPC .. A61K 38/215; A61K 38/21; A61K 2300/00; C07K 14/565
See application file for complete search history.

(56) References Cited

U.S. PATENT DOCUMENTS

| | | |
|---|---|---|
| 4,456,748 A | 6/1984 | Goeddel |
| 4,695,543 A | 9/1987 | Sloma |
| 4,738,931 A | 4/1988 | Sugano et al. |
| 4,970,161 A | 11/1990 | Kakutani et al. |
| 5,071,761 A | 12/1991 | Meyer et al. |
| 5,231,176 A | 7/1993 | Goeddel et al. |
| 5,605,688 A | 2/1997 | Himmler et al. |
| 5,641,656 A | 6/1997 | Sekellick et al. |
| 2006/0276756 A1 | 12/2006 | Francavilla |
| 2007/0292391 A1 | 12/2007 | Samaritani |
| 2010/0094205 A1 | 4/2010 | Boyd |
| 2012/0114646 A1 | 5/2012 | Tchessalov |

FOREIGN PATENT DOCUMENTS

| | | |
|---|---|---|
| JP | 2009045140 A | 3/2009 |
| JP | 2010-513309 A | 4/2010 |
| WO | 9828007 | 7/1998 |
| WO | 2008/076819 A2 | 6/2008 |

OTHER PUBLICATIONS

Bayas, A., et al., "Managing the Adverse Effects of Interferon-β Therapy in Multiple Sclerosis," Drug Safety Feb. 2000 22 (2): 149-159.
Brandes, D. W., et al., "Alleviating Flu-like Symptoms with Dose Titration and Analgesics in MS Patients on Intramuscular Interferon beta-1a Therapy: a pilot study," Current Medical Research and Opinions, vol. 23, No. 7, 1667-1672 (2007).
Frohman, E., et al., "Disease-Modifying Therapy in Multiple Sclerosis: Strategies for Optimizing Management," Neurologist, 8:227-236 (2002).
Rice, G.P.A., et al., "Ibuprofen Treatment versus Gradual Introduction of Interferon β-1b in Patients with MS," Neurology, 52:1893-1895 (1999).
Walther, E.U., et al., "Multiple Sclerosis Side Effects of Interferon beta Therapy and their Management," Neurology 53:1622-1627 (1999).
Wroe, SJ, et al., "Effects of Dose Titration on Tolerability and Efficacy of Interferon Beta-1b in People with Multiple Sclerosis," The Journal of International Medical Research, 33: 309-318 (2005).
PCT International Search Report and Written Opinion, issued in PCT/US2012/029201 dated Jun. 27, 2012, 16 pages.
"Betaferon," XP002677736, Retrieved from the Internet: URL:http://www.pharmaline.co.il/images/newsletterregistration/bayer/bataferondoctor.pdf [retrieved on Jun. 13, 2012] (Feb. 8, 2010).
"Instructions for Use: Avostartgrip Titration Kit," Biogen Idec Inc., XP002677737, Retrieved from the Internet: URL:http://www.avonex.com/pdfs/guides/Avostartgrip_IFU.pdf [retrieved on Jun. 13, 2012] (Feb. 2012).
"Medication Guide Appendix: Instructions for Preparing and Giving a Dose with an AVONEX Prefilled Syringe," Biogen Idec Inc., XP002677734, Retrieved from the Internet: URL:http://www.avonex.com/pdfs/guides/Liquid_appendix_161023.pdf [retrieved on Jun. 13, 2012] (Aug. 2010).

(Continued)

*Primary Examiner* — Karen S. Weiler
*Assistant Examiner* — Bruce D. Hissong
(74) *Attorney, Agent, or Firm* — Rothwell, Figg, Ernst & Manbeck P.C.

(57) ABSTRACT

The present invention provides a method for treating multiple sclerosis (MS), and for reducing flu-like symptoms associated with administration of an interferon to a patient with MS. The method involves intramuscularly administering the interferon to the MS patient according to an escalating dosing regimen in weeks 1 to 3, and a full therapeutically effective dose of interferon in week 4. In one embodiment of the invention, the escalating dosing regimen comprises administering one quarter of the therapeutically effective dose in week 1, half of the therapeutically effective dose in week 2, and three-quarters of the therapeutically effective dose in week 3. Also provided are titration packages for enabling compliance with a regimen of changing dosage of an interferon over a period of time.

19 Claims, 9 Drawing Sheets

(56) References Cited

OTHER PUBLICATIONS

Barrie J. Hurwitz, et al., "Tolerability and Safety Profile of 12- to 28-Week Treatment with Interferon Beta-1b 250 and 500 μg QOD in Patients with Relapsing-Remitting Multiple Sclerosis: A Multicenter, Randomized, Double-Blind, Parallel-Group Pilot Study," Clinical Therapeutics, vol. 30, No. 6, pp. 1102-1112 (Jun. 1, 2008).
Mark A. Matson, et al., "Does titration of intramuscular interferon beta-1a reduces the severity and incidence of flu-like symptoms during treatment initiation," Current Medical Research & Opinion, vol. 27, No. 12, pp. 2271-2278 (Dec. 1, 2011).
J. Theodore Phillips, et al., "A Multicenter, Open-Label, Phase II Study of the Immunogenicity and Safety of a New Prefilled Syringe (Liquid) Formulation of Avonex in Patients with Multiple Sclerosis," Clinical Therapeutics, vol. 26, No. 4, pp. 511-521 (Apr. 1, 2004).
Jacobs et al., Intramuscular interferon beta-1a for disease progression in relapsing multiple sclerosis. Annals of Neurology, 1996, vol. 39, No. 3, pp. 285-294.
Panitch, et al., "Treatment of multiple-sclerosis with gamma interferon: exacerbations associated with activation of theimmune system", Neurology, 1987, vol. 37, No. 7, pp. 1097-1102.
Singapore Written Opinion issued in SG 2013069018 dated Dec. 26, 2014, 16 pages.
Japanese Office Action dated Jan. 5, 2016, English translation attached, JP Application No. 2013-558168, 10 pages.
Japanese Office Action dated Sep. 13, 2016, issued in Japanese Application No. 2013-558168, English translation attached, 12 pages.
Examination Report No. 2 dated Nov. 28, 2016 issued by the Australian Patent Office in counterpart application 2012229104 (5 pages).
"AVONEX® (Interferon beta-1a) IM Injection". 2006. Retrieved from the Internet on Nov. 28, 216: URL: www.accessdata.fda.gov/drugsatfda_docs/label/2007/103628s5115lbl.pdf (39 pages).
"History of Changes for Study: NCT01119677, A Study of Avonex to Determine the Effects of Dose Titration on the Incidence of Flue Like Symptoms in Healthy Volunteers," ClinicalTrials.gov archive, final update, 7 pages (May 7, 2010).
"Medication Guide, AVONEX® Interferon beta-1a," Biogen, Inc., 10 pages (May 2003).
Korean Office Action issued in KR 10-2013-7027053 dated Jul. 19, 2018, including English language translation, 8 pages.

Titration Schedules

| Treatment Group | Titration Schedule | Doses of Weekly Avonex IM Injection | | | | | | | |
|---|---|---|---|---|---|---|---|---|---|
| | | 1 | 2 | 3 | 4 | 5 | 6 | 7 | 8 |
| 1 | No titration | Full dose 30 mcg | Full dose 30 mcg | Full dose 30 mcg | Full dose 30 mcg | Full dose 30 mcg | Full dose 30 mcg | Full dose 30 mcg | Full dose 30 mcg |
| 2 | Fast titration | Quarter dose 7.5 mcg | Half dose 15 mcg | Three Quarter dose 22.5 mcg | Full dose 30 mcg | Full dose 30 mcg | Full dose 30 mcg | Full dose 30 mcg | Full dose 30 mcg |
| 3 | Slow titration | Quarter dose 7.5 mcg | Quarter dose 7.5 mcg | Half dose 15 mcg | Half dose 15 mcg | Three Quarter dose 22.5 mcg | Three Quarter dose 22.5 mcg | Full dose 30 mcg | Full dose 30 mcg |
| All Groups | Prophylactic Medication: At each dosing visit, acetaminophen 650mg PO will be given within 1 hour prior to the Avonex injection, and at 4 to 6 hours, 8 to 10 hours, and 12 to 15 hours after the injection. | | | | | | | | |

FIG. 2

Primary Endpoint: FLS score

- Each symptom (muscle aches, chills, and fatigue) assigned a score from 0 to 3 by the Investigator as follows:
  - 0 = Absent
  - 1 = Mild, did not interfere with daily activities
  - 2 = Moderate, sufficient to interfere with daily activities
  - 3 = Severe, bed rest required
- Body temperature will be recorded to determine presence of fever using the following scale:
  - 0 (<99.1°F)
  - 1 (≥99.1 but <100.1°F)
  - 2 (≥100.1 but <101.1°F)
  - 3 (≥101.1°F)
- Total FLS assessment scoring
  - The total score (sum of the 3 symptom scores and the fever score) for each of the 3 timepoints (pre-injection, 4 to 6 hours, and 12 to 15 hours) calculated during data analysis.
  - A total score of 2 points or greater above the pre-injection score will be considered to be positive for presence of FLS.

FIG. 3

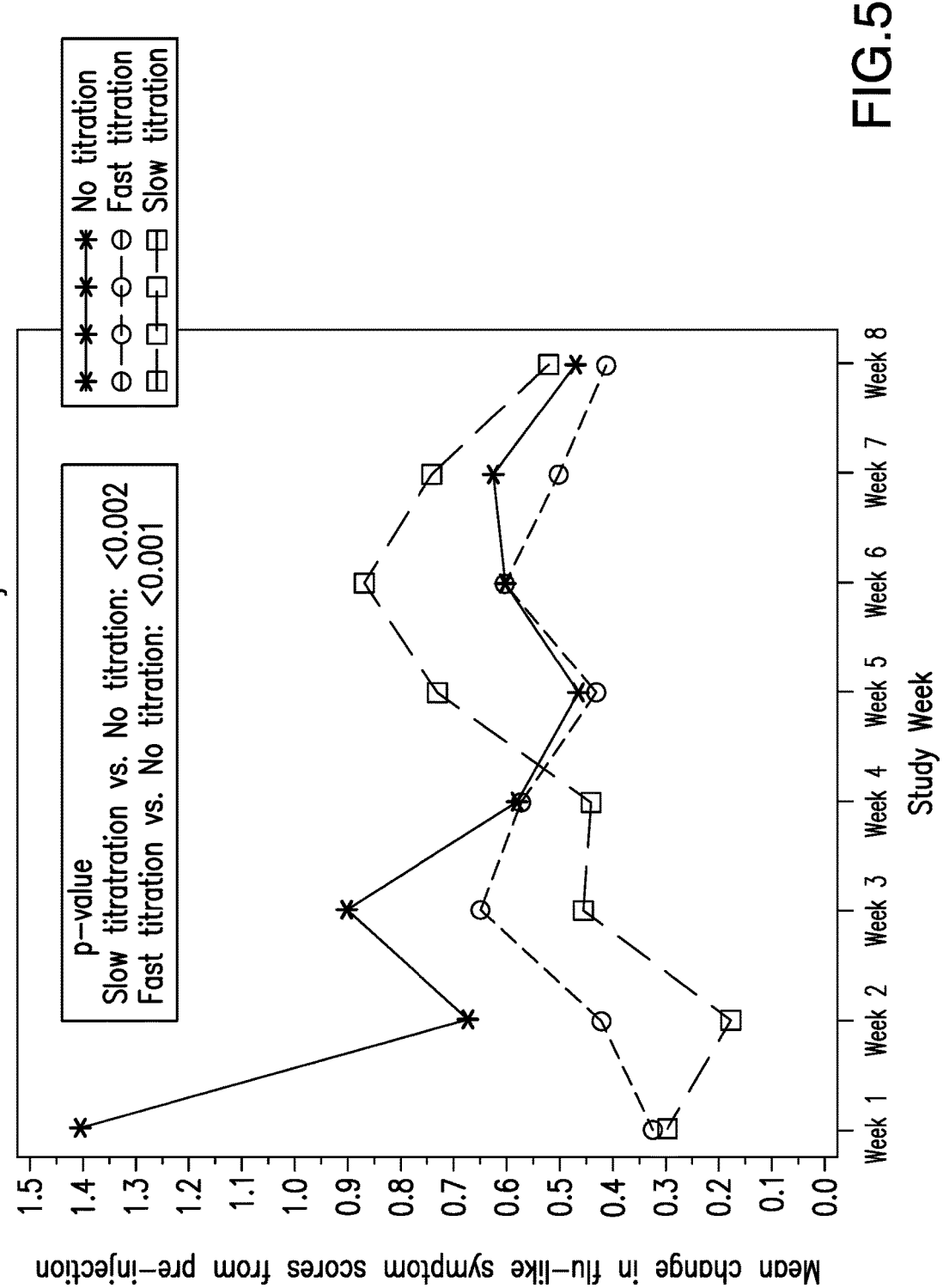

Secondary Outcome Variable: The incidence of FLS (Δ score ≥ 2) at 4 to 6 hours and at 12 to 15 hours after injection over 8 weeks Odds ratio of incidence of flu-like symptoms (total score >=2 over pre-injection) over 8 weeks – LOCF analysis

| | No titration | Fast titration | Slow titration |
|---|---|---|---|
| Number of subjects dosed | 78 (100) | 78 (100) | 78 (100) |
| Time A (4 to 6 hours post-injection) | | | |
| Odds ratio [95% CI] | | 0.179 [ 0.075, 0.429] | 0.414 [ 0.194, 0.884] |
| p-value (a) | | <0.001 | 0.023 |
| Time B (12 to 15 hours post-injection) | | | |
| Odds ratio [95% CI] | | 0.469 [ 0.272, 0.807] | 0.562 [ 0.338, 0.936] |
| p-value (a) | | 0.006 | 0.027 |

NOTE 1: Numbers in parentheses are percentages.
2: Missing values were imputed using last observation carried forward (LOCF).
(a) Odds ratio [95% CI] and p-value were from Generalized Estimating Equations method analyzing the overall treatment difference on the repeated measures over 8 weeks. The odds ratio was estimated using No titration group as the control group.

FIG.6

| | No titration | Fast titration | Slow titration |
|---|---|---|---|
| Number of subjects dosed | 78 (100) | 78 (100) | 78 (100) |
| Time A (4 to 6 hours post-injection) | | | |
| LS means | 0.539 [0.425, 0.652] | 0.132 ( 0.018, 0.245] | 0.267 [ 0.153, 0.380] |
| Difference of LS means [95% CI] | | −0.407 [−0.566, −0.248] | −0.272 (−0.431, −0.113] |
| p-value (a) | | <0.001 | <0.001 |
| Time B (12 to 15 hours post-injection) | | | |
| LS means | 0.753 [0.645, 0.861] | 0.475 [ 0.367, 0.583] | 0.515 ( 0.407, 0.623) |
| Difference of LS means [95% CI] | | −0.278 [−0.430, −0.126] | −0.238 (−0.390, −0.086] |
| p-value (a) | | <0.001 | 0.002 |

NOTE 1: Numbers in parentheses are percentages.
2: Missing values were imputed using last observation carried forward (LOCF).
(a) LS means (95% CI] and p-value were from Mixed model analyzing the overall treatment difference on the repeated measures over 8 weeks. The difference of LS means was estimated using No titration group as the control group.

FIG.7

Change in FLS at 4-6 Hours by Weeks

|  | No Titration | No Titration |
|---|---|---|
| Number of subjects dosed | 78 (100) | 78 (100) |
| Week 1 - 2 | | |
| n | 78 | 78 |
| Mean | 0.74 | 0.15 |
| SD | 1.127 | 0.303 |
| Median | 0.50 | 0.00 |
| Min, Max | 0.0, 7.0 | 0.0, 1.5 |
| p-value (a) | | <0.001 |
| Week 3 - 4 | | |
| n | 78 | 78 |
| Mean | 0.49 | 0.18 |
| SD | 1.013 | 0.386 |
| Median | 0.00 | 0.00 |
| Min, Max | 0.0, 7.0 | 0.0, 2.0 |
| p-value (a) | | 0.012 |

NOTE 1: Numbers in parentheses are percentages.
2: Missing values were imputed using last observation carried forward (LOCF).
(a) p-value from ANOVA.

FIG.9

METHOD FOR REDUCING FLU-LIKE SYMPTOMS ASSOCIATED WITH INTRAMUSCULAR ADMINISTRATION OF INTERFERON USING A FAST TITRATION ESCALATING DOSING REGIMEN

CROSS REFERENCE TO RELATED APPLICATION(S)

This application is a continuation of U.S. patent application Ser. No. 14/936,228, filed Nov. 9, 2015, which in turn is a division of U.S. patent application Ser. No. 13/421,197, filed Mar. 15, 2012, now U.S. Pat. No. 9,198,955, issued on Dec. 1, 2015, which in turn is a nonprovisional of U.S. provisional patent application Ser. No. 61/452,807, filed Mar. 15, 2011 and U.S. provisional patent application Ser. No. 61/476,930, filed Apr. 19, 2011. The disclosure of each application is incorporated herein in its entirety by reference.

BACKGROUND OF THE INVENTION

Field of the Invention

The present invention relates generally to a method for treating multiple sclerosis (MS), and for reducing flu-like symptoms generally associated with administration of interferons. In particular, the method uses a fast-titration escalating dosing regimen of intramuscularly administered interferon. The invention also relates to titration packaging to promote compliance with the dosage titration.

Description of Related Art

Multiple sclerosis (MS) is a chronic neurological and inflammatory disorder of the central nervous system, marked by focal autoreactive T-cell and macrophage infiltration through the blood brain barrier that lead to demyelination, and axonal and neuronal loss. In people affected by MS, patches of damage called plaques or lesions appear in seemingly random areas of the CNS white matter. At the site of a lesion, a nerve insulating material, myelin, is lost in demyelination. Inflammation, demyelination, oligodendrocyte death, membrane damage and axonal death all contribute to the symptoms of MS.

Although MS has an unknown etiology, the classical hypothesis is that MS is a T helper 1 (TH1)-cell mediated autoimmune disease. Development of lesions is characterized by accumulation of activated microglia and macrophages. Acute plaques are characterized by blood brain barrier damage, infiltration by activated CD4+ T cells and clonotypic CD8+ T cells that recognize CNS autoantigens, and the presence of reactive astrocytes and proliferating oligodendrocytes. Pro-inflammatory cytokines, e.g. interleukin 12 (IL-12) and tumour-necrosis factor-a (TNF-a), are also present. There is further evidence that other adaptive immune cells (e.g. TH17 cells and peripheral B lymphocytes) and innate immune cells (dendritic cells, natural killer T cells and resident microglia) play a role in MS pathogenesis.

Relapse-remitting MS, the most common form of the disease, is characterized by multiple exacerbations over time. Exacerbations are attacks on vision, motor, sensory, and sphincter control and cognitive processes. Patients with relapse-remitting MS do not completely recover from these exacerbations and accrue neurologic disability with each subsequent exacerbation.

Natural human fibroblast interferon-beta (IFN-$\beta$) was the first drug to treat relapse-remitting MS. IFN-$\beta$ has immunomodulatory effects, which include modulating cytokine levels (e.g., inducing Th1 (T-helper 1) related cytokines and Th2 related cytokines), inhibiting T-cell activation and proliferation, inhibiting transmigration of autoreactive T cells into the CNS, increasing T cell apoptosis, and reducing expression of molecules required for antigen presentation. IFN-$\beta$ has well-established clinical effects and studies evidence that IFN-$\beta$ works against multiple sclerosis through immunomodulation.

There are currently two different recombinant interferon-beta treatments for MS: interferon beta-1a (IFN-$\beta_{1a}$) and interferon beta-1b (IFN-$\beta_{1b}$). IFN-$\beta_{1a}$ and IFN-$\beta_{1b}$ are two distinct molecules with different recommended dosages, routes of administration and dosing intervals. IFN-$\beta_{1a}$ is a 166 amino acid glycoprotein with a predicted molecular weight of approximately 22,500 daltons. It is produced by recombinant DNA technology using genetically engineered Chinese Hamster Ovary cells into which the human interferon beta gene has been introduced. The amino acid sequence is identical to that of natural human interferon beta. IFN-$\beta_{1b}$ has 165 amino acids and an approximate molecular weight of 18,500 daltons. It does not include the carbohydrate side chains found in the natural material. IFN-$\beta_{1b}$ is manufactured by bacterial fermentation of a strain of *Escherichia coli* that bears a genetically engineered plasmid containing the gene for human interferon beta$_{ser17}$. The specific activity of IFN-$\beta_{1a}$ and IFN-$\beta_{1b}$ are different and based on different World Health Organization (WHO) reference standards of recombinant interferon beta and different assays used to measure activity.

Current IFN-$\beta_{1a}$ treatments include Avonex®, CinnoVex™, Rebif®, and Resigene. Current IFN-$\beta_{1b}$ treatments include Betaseron® in the US and Betaferon® in Europe, and Extavia®. Avonex® and CinnoVex™ are administered intramuscularly, while the other interferon treatments for MS are administered subcutaneously.

Although there is a difference in specific activity between the two types of interferons, IFN-$\beta_{1a}$ and IFN-$\beta_{1b}$ share similar side effect profiles. For example, a common adverse event associated with interferon therapies are flu-like symptoms that develop within a few hours after administration and subside within 24 hours. Flu-like symptoms associated with administration of interferons include fever, muscle aches (myalgia), chills, sweating, fatigue, headache, and malaise. The exact mechanism for the development of flu-like symptoms is not well understood but occurs among patients taking interferons irrespective of disease state. It has been postulated that interferons stimulate the sub-thalamic nucleus, thus affecting temperature, as well as local cytokines resulting in other symptoms.

Generally, the flu-like symptoms will significantly decrease after 2-3 months. However, flu-like symptoms associated with interferon administration at the beginning of treatment can be a significant barrier to the initiation or maintenance of MS therapy, even before the onset of any therapeutic benefit. Use of an escalating dosing regimen (also known as dose titration) has become a routine practice for the administration of interferon therapies to manage side effects at the initiation of therapy. The goal of dose titration is to improve the acceptance and adherence of therapy and, thus, impact long-term health benefits for patients with multiple sclerosis. Currently, there are only two interferon-beta products, Betaseron® and Rebif®, that provide dose titration instructions in their labels. Both Betaseron® and Rebif® are administered subcutaneously.

The Betaseron® (December 2007) label includes titration instructions for subcutaneous administration of IFN-$\beta_{1b}$ over a six-week period, with full dose beginning in week 7:

Weeks 1-2—¼ of a dose (0.0625 mg/0.25 ml)
Weeks 3-4—½ of a dose (0.125 mg/0.5 ml)
Weeks 5-6—¾ of a dose (0.1875 mg/0.75 ml)
Week 7—full dose (0.25 mg/1 ml)

The Betaseron® label indicates dose titration may reduce flu-like symptoms. The European Betaferon® label (Jan. 8, 2024) includes titration instructions for subcutaneous administration over a three week period, with full dose beginning in week 4:

Week 1—¼ of a dose (0.0625 mg/0.25 ml)
Week 2—½ of a dose (0.125 mg/0.5 ml)
Week 3—¾ of a dose (0.1875 mg/0.75 ml)
Week 4—full dose (0.25 mg/1 ml)

Although the European Betaferon® label has a three week titration period with ¼ dose increments, the label recommends dose titration at the start of treatment in order to increase tolerability and to reduce side effects, only generally, at the start of therapy. Unlike the US Betaseron® label which indicates a 6 week titration period and the possibility of a reduction in flu-like symptoms, the 3 week titration period of the European Betaferon® label is silent with respect to treating flu-like symptoms. Two clinical studies reveal that ¼ dose increments over a three-week period do not provide a significant reduction in flu-like symptoms in comparison to slow titration regimens.

Rice et al (Rice G P A, Ebers G C, Lublin F D, Knobler R L. Ibuprofen Treatment versus Gradual Introduction of Interferon beta-1b in Patients with MS. *Neurology* 52:1893-1895, 1999) evaluated the effectiveness of dose titration in combination with ibuprofen in reducing the flu-like side effects of Betaseron® administered subcutaneously in 49 patients with Relapsing-Remitting and Secondary Progressive Multiple Sclerosis (RR and SPMS). This was a randomized, open-label, study that compared patients who did not titrate Betaseron® but took ibuprofen prophylaxis (Group A), to those who titrated Betaseron® with (Group B) and without Ibuprofen treatment (Group C). Group A received 8 million IU (MIU) of Betaseron® every second day (the standard dose) during weeks 0-4. Groups B and C each received Betaseron® according to the titration schedule starting at 2 MIU (25% of the standard dose) and increased at increments of 2 MIU (25% of the standard dose) during weeks 0-4. During weeks 0-4, 11% (2 out of 18) of Group A patients developed flu-like symptoms, 6% (1 out of 6) of Group B patients developed flu-like symptoms, and 40% of Group C patients developed flu-like symptoms (Table 1 of Rice et al.). The differences in incidence of flu-like symptoms between the group receiving ibuprofen treatment alone (Group A) and the group receiving dosage escalation and ibuprofen treatment (Group B) does not appear to be significant.

Moreover, Rice et al. reported that 5 (three from Group A, one from Group B, and one from Group C) of the 49 patients (10%) in the study experienced difficulty while escalating the dose of IFN-$\beta_{1b}$, and these patients required either dosage reduction or a delay in the escalating schedule.

This was common practice according to Bayas et al. (Bayas A and Rieckmann P. Managing the Adverse Effects of Interferon-β Therapy in Multiple Sclerosis. *Drug Safety* 22(2):149-159, 2000). Bayas et al. described dose titration for administration of IFN-$\beta_{1b}$ (which is only administered subcutaneously) where treatment began at 20 to 25% dose for 1 week, increased to 50% dose the second week, and if treatment was tolerated, increased to full dose. According to Bayas et al., interferon-β dosage should be reduced or kept at the same level for a longer time until improved drug tolerability allows an increase. Walther et al. (Walther E U, Hohlfeld R. Multiple Sclerosis Side Effects of Interferon beta Therapy and their Management. *Neurology* 53:1622-1627, 1999) recommended one dose reduction (between 25-50%) that should be maintained, rather than escalated, for 4-6 weeks. Thus, it was common practice to err on the side of an extended titration schedule.

Wroe (Wroe S J. Effects of dose titration on tolerability and efficacy of interferon beta-1b in people with multiple sclerosis. *J Int Med Res* 33:309-18, 2005) evaluated whether a slower, four-stage, 4 week titration to a final dose of 250 µg subcutaneous IFN-$\beta_{1b}$ might improve tolerability over a more rapid two-stage, 2 week titration in patients with relapsing-remitting MS over a 3-month period. In the slow-titration group, IFN-$\beta_{1b}$ was subcutaneously administered, initially at 62.5 µg (¼ dose) every other day for 9 days, and then at ¼ dose increments (125 µg and 187.5 µg, respectively) on days 11 and 21, and a full dose (250 µg) beginning on day 31 (i.e. in the middle of week 5) for the remainder of the 3-month treatment. See FIG. 1 of Wroe et al. In the fast-titration group, IFN-$\beta_{1b}$ was subcutaneously administered, initially at 125 µg (½ dose) every other day for 2 weeks and then at full dose for the remainder of the 3-month treatment. One of the primary adverse events assessed was flu-like symptoms. Wroe reported no noticeable differences with respect to the occurrence of adverse events between the two treatment groups, e.g., the incidence rates of flu-like symptoms were similar in the slow—(32.4%) and rapid titration (41.9%) groups (FIG. 3 of Wroe et al). Wroe concluded that a rapid-titration regimen (½ dose increments, with a full dose beginning in week 3) results in a quicker onset of clinical benefit and slow titration (¼ dose increments, with a full dose beginning in the middle of week 5) showed a non-significant reduction in flu-like symptoms compared to the rapid-titration regimen.

The Rebif® label includes titration instructions for subcutaneous administration of IFN-$\beta_{1a}$ three times per week over a 4-week period, with full dose administered in week 5:

Weeks 1-2—⅕ of a dose—subcutaneous injection 3×/week
  (titration dose for 33 µg=4.4 µg)
  (titration dose for 44 µg=8.8 µg)
Week 3-4—½ of a dose—subcutaneous injection 3×/week
  (titration dose for 33 µg=11 µg)
  (titration dose for 44 µg=22 µg)
Week 5—full dose—subcutaneous injection 3×/week The European Rebif® label recommends a gradual increase during a 4 week period to reduce adverse reactions. The ⅕ dose during the first two weeks serves the purpose of allowing tachyphylaxis to develop, thus reducing side effects. Both the US and European labels are silent with respect to treating flu-like symptoms associated with administration of interferon-beta. All of the products and clinical studies discussed thus far relate to subcutaneous administration of IFN-$\beta_{1a}$ or IFN-$\beta_{1b}$.

Brandes et al. (Brandes D W, Bigley K, Hornstein W, Cohen H, Au W, Shubin R. Alleviating Flulike Symptoms with Dose Titration and Analgesics in MS Patients on Intramuscular Interferon beta-1a Therapy: a pilot study. *Curr Med Research and Opinions* 23(7):1667-1672, 2007), appears to be the first to investigate dose titration of intramuscular administration (IM) of IFN-$\beta_{1a}$. Brandes et al. evaluated the effectiveness of dose titration in combination with acetaminophen or ibuprofen in reducing the flu-like side effects of Avonex® (IFN-$\beta_{1a}$) in 47 patients with relapsing-remitting multiple sclerosis.

The Brandes et al. study was a multi-site, randomized, open-label, 12-week study. Group 1 patients received (IM) IFN-$\beta_{1a}$ at a dose of 30 μg once weekly with no titration. Groups 2 and 3 received (IM) IFN-$\beta_{1a}$ at ¼ dose during weeks 1 and 2, ½ dose for weeks 3 and 4, ¾ dose at weeks 5 and 6, and a full dose (30 μg) for weeks 7-12. Groups 1 and 2 received acetaminophen 650 mg 1 hour before each (IM) IFN-$\beta_{1a}$ injection, then every 4 hours as needed. Group 3 received ibuprofen 400 mg 1 hour before each (IM) IFN-$\beta_{1a}$ injection, again at 6 hours following injection, then every 6 hours as needed. Flu-like symptoms were recorded at three time points: baseline (first dose of analgesic, 1 hour pre-injection); Time A (second dose of analgesic, 4 hours post-injection); and Time B (12-15 hours post-injection).

Brandes et al. found that one-quarter titration (Groups 2 and 3) significantly reduced the proportion of patients with a mean increase of ≥2 from baseline in flu-like symptom score compared with no titration only at 4 hours post-injection during the first two weeks (FIG. 1A of Brandes et al., p=0.015 indicated with *). There was no significant difference between the one-quarter titration (Groups 2 and 3) and no titration (Group 1) at 4 hours during weeks 3-12 as the dose was increased. These data suggested that a ¼ dose escalation does not reduce flu-like symptoms, suggesting that further prolonged titration, i.e., an even slower titration, would be necessary.

Also, there was no significant difference between the one-quarter titration (Groups 2 and 3) and no titration (Group 1) at 12-15 hours during any week, including the first two weeks. These data suggested that initiating (IM) IFN-$\beta_{1a}$ injection with a ¼ dose had limited effects in reducing flu-like symptoms because the ¼ dose only delayed the onset of flu-like symptoms and only did so during the first two weeks.

Frohman et al (Frohman E et al. Disease-Modifying Therapy in Multiple Sclerosis: Strategies for Optimizing Management. *Neurologist* 8:227-236, 2002) in a comprehensive review of MS therapy management, recommends initiating treatment during the tapering phase of a steroid regimen and applying a fractionated dosing scheme in patients treated with either Avonex®, Rebif® or Betaseron® in combination with a nonsteroidal anti-inflammatory agent. In particular, patients were started at 25% of the recommended dose and dosages were increased by 25% increments weekly to every other week. Frohman et al. describes the 25% dose as "a dose usually associated with minimal to no side effects" given that interferon-related side effects are dose-response related. Significantly, Frohman et al. states, "If patients experience severe and limiting side effects as the dose is increased, we will generally prolong titration, escalating by the same increment every 2 to 4 weeks. With this approach, we have had very few patients fail drug initiation." Thus, Frohman teaches to err on the side of an extended titration schedule.

It is therefore desirable to provide a method for further reducing flu-like symptoms associated with intramuscular interferon administration, which will promote compliance and continuation of interferon therapy for MS.

SUMMARY OF THE INVENTION

The inventors have surprisingly found that by decreasing the time period of the dose titration schedule for the intramuscular administration of interferon ("fast titration"), the appearance of flu-like symptoms is significantly reduced as compared to a longer dose titration schedule ("slow titration").

As such, the present invention provides a method for treating multiple sclerosis, which includes intramuscularly administering an interferon to a patient once per week, and specifically includes an initial titration period wherein the interferon is administered in an escalating dose regimen (a "titration period"). In particular, the titration period includes a one-quarter dose in week one, a one-half dose in week two, a three-quarter dose in week 3, and a full therapeutically effective dose in week 4 and thereafter.

The present invention also provides a method for reducing flu-like symptoms associated with the administration of an interferon to a patient with multiple sclerosis, including (a) intramuscularly administering the interferon to the patient according to an escalating dosing regimen in weeks 1 to 3; and (b) intramuscularly administering a full therapeutically effective dose of interferon in week 4.

The invention also relates to a titration package for enabling compliance with these methods, wherein the dosage of interferon changes over a period of time. The titration package includes interferon delivery devices containing an interferon, and instructions for the patient to administer the interferon in an escalating dose regimen during a titration period.

The foregoing and other objects, features and advantages of the invention will be apparent from the following more particular description of preferred embodiments of the invention.

BRIEF DESCRIPTION OF THE FIGURES

The accompanying Figures, which are incorporated herein and form part of the specification, illustrate embodiments of the present invention and, together with the description, further serve to explain the principles of the invention.

FIG. 2 is a table with the titration schedules in a clinical study. Patients in Treatment Group 1 received a full intramuscular dose of Avonex® each week for 8 weeks. Patients in Treatment Group 2 received intramuscular doses of Avonex® according to a fast titration schedule (¼ dose in week 1, ½ dose in week 2, ¾ dose in week 3, and full dose in weeks 4-8). Patients in Treatment Group 3 received intramuscular doses of Avonex® according to a slow titration schedule (¼ dose in weeks 1-2, ½ dose in weeks 3-4, ¾ dose in weeks 5-6, and full dose in weeks 7-8). All patient groups received prophylactic medication.

FIG. 3 describes a method of scoring flu-like symptoms (FLS) in accordance with the invention.

FIG. 5 is a line graph of the secondary outcomes variable and shows the change in total flu-like symptom (FLS) score from pre-injection to 12 to 15 hours after injection over 8 weeks.

FIG. 6 is a table of the secondary outcome variable and provides the odds ratio of incidence of flu-like symptom (FLS) score at 4 to 6 hours and at 12 to 15 hours after injection over 8 weeks.

FIG. 7 provides data comparing the effect on flu-like symptoms of no titration, fast titration and slow titration.

FIG. 9 provides data comparing the effect on flu-like symptoms of no titration to slow titration.

DETAILED DESCRIPTION OF THE INVENTION

Figure 1:
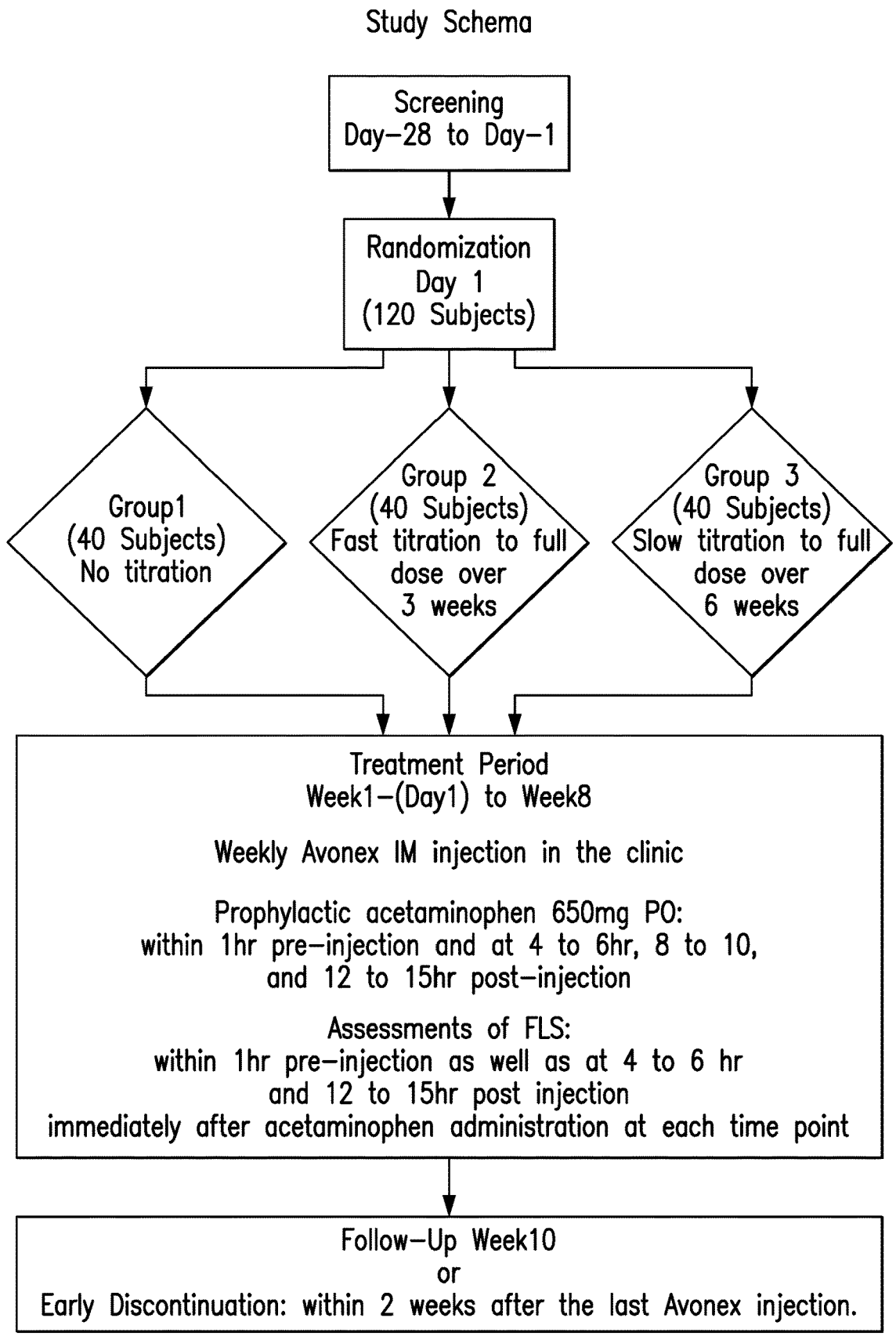
FIG. 1 is a flow chart showing the design of a "fast vs. slow" titration trial. Note that in the Example below, additional subjects were investigated.

The invention provides a method for treating a subject with multiple sclerosis, by intramuscularly administering an interferon using an initial escalating dosage regimen or titration period. Treatment is preferably once a week. The escalating dosage regimen typically involves administration of a one-quarter dose in week one, a one-half dose in week two, a three-quarter dose in week 3, and a full therapeutically effective dose in week 4 and thereafter.

In a preferred embodiment, the week one dose is about 7.5 micrograms, the week two dose is about 15 micrograms, the week three dose is about 22.5 micrograms, and the week four dose is about 30 micrograms.

In a preferred embodiment, the interferon is interferon $\beta$. In a more preferred embodiment, the interferon is an interferon $\beta_1$. In a most preferred embodiment, the interferon is interferon $\beta_{1a}$.

The invention also provides a method for reducing the flu-like symptoms which can accompany the intramuscular administration of an interferon. In particular, the invention provides a method involving the intramuscularly administration of interferon to the patient according to an escalating dosing regimen in weeks 1 to 3; and then the administration of a full therapeutically effective dose of interferon in week 4.

Reducing flu-like symptoms can be measured in reduction of severity of symptoms, and/or reduction in incidence of flu-like symptoms. The reduction can be measured at various timepoints post-injection, for example 4 to 6 hours post-injection and 12 to 15 hours post-injection.

Preferably, the reduction in severity of flu-like symptoms at 4 to 6 hours is at least 40%, more preferably at least 50%, even more preferably at least 60%, and most preferably at least 70%. The reduction in severity of flu-like symptoms at 12 to 15 hours is preferably at least 10%, more preferably at least 20%, even more preferably at least 25%, and most preferably at least 30%.

The reduction in incidence of flu-like symptoms at 4 to 6 hours is preferably at least 5%, more preferably at least 10%, even more preferably at least 15%, and most preferably about 20%. Preferably, the reduction in incidence of flu-like symptoms at 12 to 15 hours is at least 10%, more preferably at least 15%, even more preferably at least 20%, and most preferably about 25%.

In a preferred embodiment, the invention includes administering one quarter of the therapeutically effective dose in week 1, half of the therapeutically effective dose in week 2, and three-quarters of the full therapeutically effective dose in week 3.

In a most preferred embodiment, the full therapeutically effective dose is 30 micrograms.

Flu-like symptoms can include, for example, fever, muscle aches (myalgia), chills, sweating, fatigue, headache, and malaise, and can be scored in accordance with the method of FIG. 3.

The methods of the invention can further include the administration of an analgesic or anti-inflammatory drug, or a mixture thereof. The drug may be a steroid or a non-steroidal anti-inflammatory drug. Preferred drugs include acetaminophen and ibuprofen.

The invention also provides titration packages, wherein the interferon is presented in a way to promote compliance with the escalating dosage regimen, and ultimately the long-term treatment using the interferon.

In a preferred embodiment, the package includes interferon and delivery devices for the interferon. The interferon may be in lyophilized form, and thus packaged in a jar or vial. In this case, the package also preferably contains a device, such as a syringe, which is pre-filled with a diluent for lyophilized interferon.

Alternatively, the interferon may in liquid form. In this case, the interferon may be provided in pre-filled syringes. The syringes may be provided with the exact dosage for weeks 1-4 and thereafter. Alternatively, an accessory to the delivery device may also be provided, which when used in combination with the syringe, is capable of titrating the correct volume or dosage for the particular week of the escalating dosage regimen (titration period).

Where the interferon is provided in a syringe, the syringe may also be provided with a needle stick prevention device. Such a prevention device can include a needle shield, which may be automated. The shield may be completely automatic (i.e., without any action by the patient), or may be activated by the patient.

The interferon may also be provided in other delivery devices, such as a pen.

The titration package also preferably contains instructions for intramuscular administration of the interferon by a patient during a titration period, wherein the interferon is preferably administered at a one-quarter dose in week one, a one-half dose in week two, a three-quarter dose in week 3, and a full therapeutically effective dose in week 4.

The following terms are used herein:

Interferon—An "interferon" (also referred to as "IFN") is a small, species-specific, single chain polypeptide, produced by mammalian cells in response to exposure to a variety of inducers such as viruses, polypeptides, mitogens and the like. The most preferred interferon used in the invention is glycosylated, human, interferon-$\beta$ that is glycosylated at residue 80 (Asn 80) and that is preferably derived via recombinant DNA technologies. This preferred glycosylated interferon-$\beta$ is called "interferon-$\beta_{1a}$". The term "interferon-$\beta_{1a}$" is also intended to encompass all mutant forms (i.e., Example 1) provided that the mutants are also glycosylated at the Asn 80 residue.

Recombinant DNA methods for producing proteins are known.

Preferred interferon-$\beta_{1a}$ polynucleotides that may be used in the present methods of the invention are derived from the wild-type interferon $\beta$ gene sequences of various vertebrates, preferably mammals and are obtained using methods that are well-known to those having ordinary skill in the art such as the methods described in the following U.S. U.S. Pat. No. 5,641,656 (issued Jun. 24, 1997: DNA encoding avian type I interferon proprotein and mature avian type I interferon), U.S. Pat. No. 5,605,688 (Feb. 25, 1997—recombinant dog and horse type I interferons); U.S. Pat. No. 5,231,176 (Jul. 27, 1993, DNA molecule encoding a human leukocyte interferon); U.S. Pat. No. 5,071,761 (Dec. 10, 1991, DNA sequence coding for sub-sequences of human lymphoblastoid interferons LyIFN-alpha-2 and LyIFN-alpha-3); U.S. Pat. No. 4,970,161 (Nov. 13, 1990, DNA sequence coding for human interferon-gamma); U.S. Pat. No. 4,738,931 (Apr. 19, 1988, DNA containing a human interferon beta gene); U.S. Pat. No. 4,695,543 (Sep. 22, 1987, human alpha-interferon Gx-1 gene and U.S. Pat. No. 4,456,748 (Jun. 26, 1984, DNA encoding sub-sequences of different, naturally, occurring leukocyte interferons).

Mutants of interferon-$\beta_{1a}$ may be used in accordance with this invention. Mutations are developed using conventional methods of directed mutagenesis, known to those of ordinary skill in the art. Moreover, the invention provides for functionally equivalent interferon-$\beta_{1a}$ polynucleotides that encode for functionally equivalent interferon-beta-1a polypeptides.

In summary, the term "interferon" includes, but is not limited to, the agents listed above as well as their functional equivalents. As used herein, the term "functional equivalent" therefore refers to an interferon-$\beta_{1a}$ protein or a polynucleotide encoding the interferon-beta-1a protein that has the same or an improved beneficial effect on the mammalian recipient as the interferon of which it is deemed a functional equivalent. As will be appreciated by one of ordinary skill in the art, a functionally equivalent protein can be produced by recombinant techniques, e.g., by expressing a "functionally equivalent DNA". Accordingly, the instant invention embraces interferon-$\beta_{1a}$ proteins encoded by naturally-occurring DNAs, as well as by non-naturally-occurring DNAs which encode the same protein as encoded by the naturally-occurring DNA. Due to the degeneracy of the nucleotide coding sequences, other polynucleotides may be used to encode interferon-$\beta_{1a}$. These include all, or portions of the above sequences which are altered by the substitution of different codons that encode the same amino acid residue within the sequence, thus producing a silent change. Such altered sequences are regarded as equivalents of these sequences. For example, Phe (F) is coded for by two codons, TTC or TTT, Tyr (Y) is coded for by TAC or TAT and His (H) is coded for by CAC or CAT. On the other hand, Trp (W) is coded for by a single codon, TGG. Accordingly, it will be appreciated that for a given DNA sequence encoding a particular interferon there will be many DNA degenerate sequences that will code for it.

The interferon may be administered per se as well as in the form of pharmaceutically acceptable esters, salts, and other physiologically functional derivatives thereof. In such pharmaceutical and medicament formulations, the interferon preferably is utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The interferon is provided in an amount effective to achieve the desired pharmacological effect, as described above, and in a quantity appropriate to achieve the desired daily dose.

The formulations include those suitable for intramuscular administration.

The formulations may conveniently be presented in unit dosage forms and may be prepared by any of the methods well known in the art of pharmacy. Such methods generally include the step of bringing the active ingredient(s) into association with a carrier which constitutes one or more accessory ingredients. Typically, the formulations are prepared by uniformly and intimately bringing the active ingredient(s) into association with a liquid carrier.

The formulations may be presented in unit-dose or multi-dose form.

In addition to the aforementioned ingredients, the formulations may further include one or more accessory ingredient(s) selected from diluents, buffers, disintegrants, surface active agents, thickeners, lubricants, preservatives (including antioxidants), and the like.

In yet more detail, the present invention is described by the following items which represent additional embodiments hereof.

1. A method for treating multiple sclerosis, including intramuscularly administering an interferon to a patient once per week, wherein treatment begins with a titration period wherein the interferon is administered at a one-quarter dose in week one, a one-half dose in week two, a three-quarter dose in week 3, and a full therapeutically effective dose in week 4 and thereafter.

2. The method of item 1, wherein the week one dose is about 7.5 micrograms, the week two dose is about 15 micrograms, the week three dose is about 22.5 micrograms, and the week four dose is about 30 micrograms.

3. The method of item 1, wherein the interferon is interferon $\beta_{1a}$.

4. A method for reducing flu-like symptoms associated with administration of an interferon to a patient with multiple sclerosis, including:
   (a) intramuscularly administering the interferon to the patient according to an escalating dosing regimen in weeks 1 to 3; and
   (b) intramuscularly administering a full therapeutically effective dose of interferon in week 4.

5. The method of item 4, wherein the escalating dosing regimen comprises administering one quarter of the therapeutically effective dose in week 1, half of the therapeutically effective dose in week 2, and three-quarters of the therapeutically effective dose in week 3.

6. The method of item 4, wherein the interferon is interferon $\beta_{1a}$.

7. The method of item 4, wherein the full therapeutically effective dose is 30 micrograms.

8. The method of item 4, wherein the flu-like symptoms include fever, muscle aches, chills, sweating, fatigue, headache, and malaise.

9. A titration package for enabling compliance with a regimen of changing dosage of an interferon over a period of time, the package including interferon delivery devices containing an interferon and instructions for administration by a patient during a titration period, wherein the interferon is administered at a one-quarter dose in week one, a one-half dose in week two, a three-quarter dose in week 3, and a full therapeutically effective dose in week 4.

10. The titration package of item 9, wherein the instructions indicate a week one dosage of about 7.5 micrograms, a week two dose of about 15 micrograms, a week three dosage of about 22.5 micrograms, and a week four dosage of about 30 micrograms.

11. The titration package of item 9, wherein the interferon is provided in a vial in lyophilized form.

12. The titration package of item 11, further comprising a vial adapter and a syringe pre-filled with a diluent for said lyophilized interferon.

13. The titration package of item 9, wherein the interferon is provided in a liquid formulation.

14. The titration package of item 13, wherein the liquid interferon formulation is provided in pre-filled syringes.

15. The titration package of item 14, wherein the pre-filled syringes are filled with a correct dosage for weeks one to four.

16. The titration package of item 9, wherein the delivery device comprises an auto-injector.

17. The titration package of item 9, wherein the delivery device is needle-free.

18. The titration package of item 9, wherein the deliver device is a pen.

19. The titration package of item 9, further comprising a needle stick prevention device.

20. The titration package of item 19, wherein the needle-stick prevention device includes a needle shield.

21. The titration package of item 20, wherein the shield is activated manually by the patient.

22. The titration package of item 20, wherein the shield is automated.

23. The titration package of item 22, wherein the automated shield is activated by the patient.

24. The titration package of item 22, wherein the needle is automatically shielded without any action by the patient.

25. The titration package of item 22, wherein the needle is shielded without any action by the patient.

26. The titration package of item 9, wherein the package further includes a dose-limiting titration device.

27. The method of any of items 1-8, further comprising administration of an analgesic or anti-inflammatory drug, or a mixture thereof.

28. The method of item 27, wherein the drug is a steroid.

29. The method of item 27, wherein the drug is a non-steroidal anti-inflammatory agent.

30. The method of item 27, wherein the drug is acetaminophen.

31. The method of item 27, wherein the drug is ibuprofen.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Avonex® was studied in a randomized, three-arm, dose-blinded, parallel-group study to determine the effect of Avonex® dose titration, administered intramuscularly, on the severity and incidence of IFN-$\beta_{1a}$-related flu-like symptoms in healthy volunteers. The approved therapeutic dose of Avonex® is 30 µg weekly by IM administration.

In this blinded, parallel-group study, subjects were randomized to 1 of 3 treatment arms: Group 1—no titration (weekly IM IFN-$\beta_{1a}$ 30 µg for 8 weeks); Group 2—fast dose titration (quarter-dose increments every week up to 30 µg over 3 weeks, full dose to Week 8); and Group 3—slow dose titration (quarter-dose increments every 2 weeks up to 30 µg over 6 weeks, full dose to Week 8). See FIG. 1. In order to evaluate flu-like symptoms (FLS) in a controlled condition and to avoid bias, all subjects, regardless of symptoms, were administered prophylactic medication (acetaminophen 650 milligrams (mg) orally within 1 hour prior to Avonex® injection, and at 4 to 6 hours, 8 to 10 hours, and 12 to 15 hours following injection.)

Each week, the presence and intensity of fever, muscle aches (myalgia), chills, and fatigue symptoms were recorded at pre-injection, 4 to 6 hours and 12 to 15 hours post injection. Each FLS was assigned a score from 0 to 3 by the investigator as follows: 0=absent; 1=mild, did not interfere with daily activities; 2=moderate, sufficient to interfere with daily activities; 3=severe, bed rest required. Body temperature was recorded to determine the presence of fever using the following scale: 0 (<99.1° F.); 1 (≥99.1° F. but <100.1° F.); 2 (≥100.1° F. but <101.1° F.); 3 (≥101.1° F.). The total score (sum of the 3 symptom scores and fever score) for each of the 3 timepoints (pre-injection, 4 to 6 hours, and 12 to 15 hours) was be calculated during data analysis. For each timepoint, the maximum total score was 12 and the minimum total score was 0. A total score of 2 points or greater above the pre-injection score was considered positive for the presence of FLS.

Figure 4:
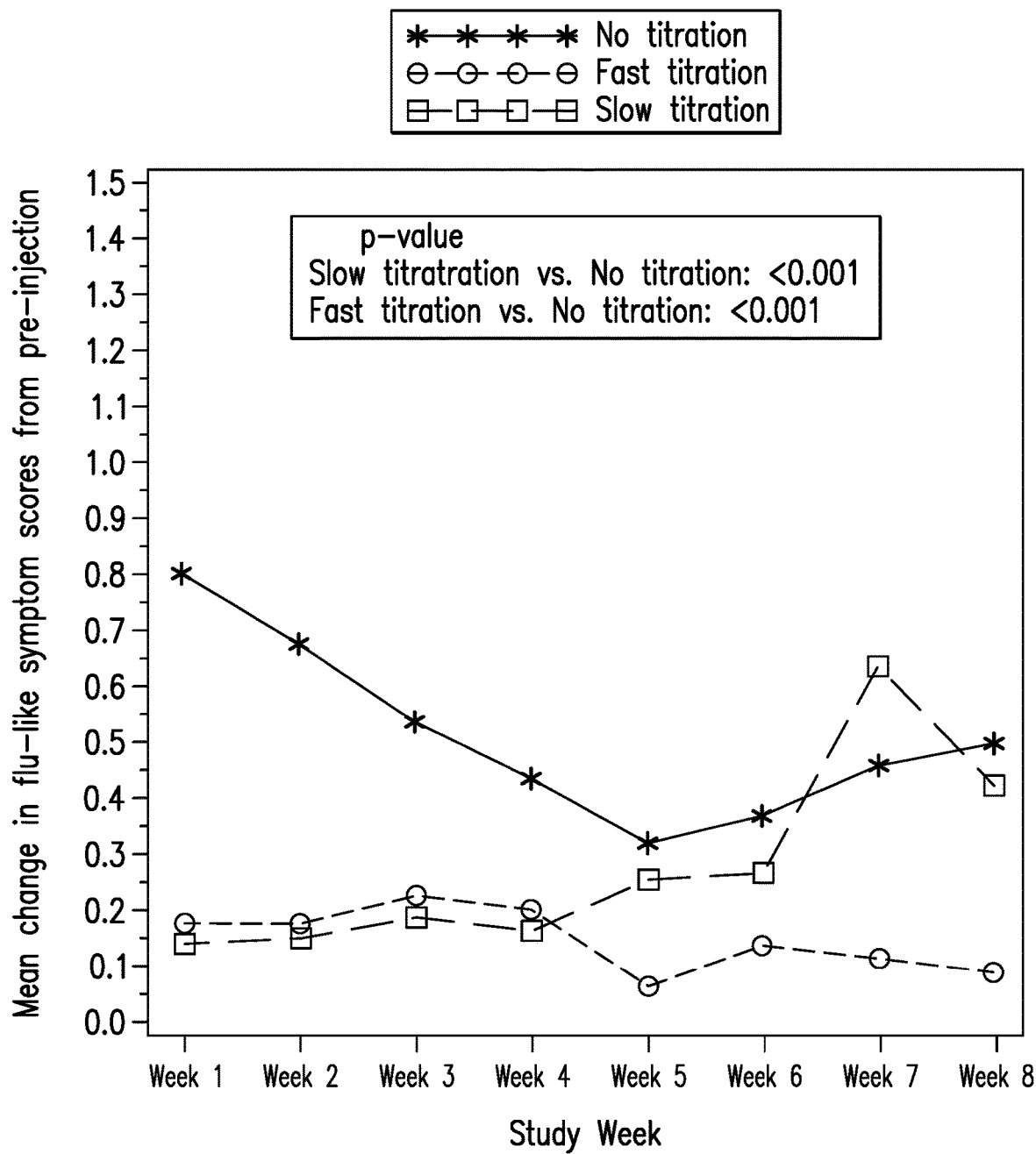
FIG. 4 is a line graph of the primary outcome variable and shows the change in total flu-like symptom (FLS) score from pre-injection to 4 to 6 hours after injection over 8 weeks.
Figure 8:
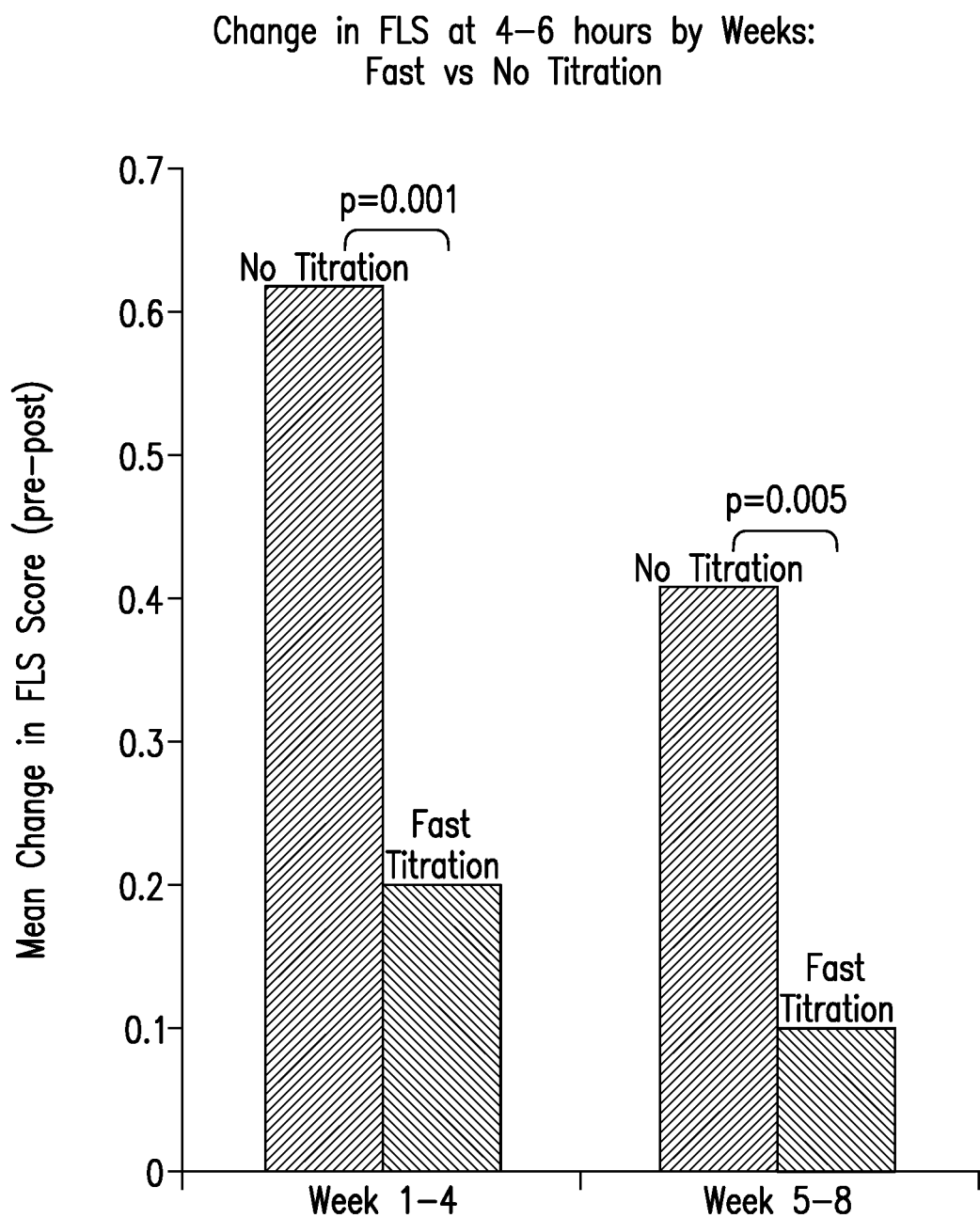
FIG. 8 is a bar graph comparing the change in flu-like symptoms (FLS) at 4-6 hours, comparing no titration to fast titration.

A total of 234 subjects were enrolled, 78 per arm, and 195 (83%) completed the study. The majority of subjects were female (62%) and the mean age was 32.9 years. Subjects in the fast and slow titration arms had significantly less severe FLS over 8 weeks than subjects in full-dose arm at 4-6 hours post injection (0.132 [P<0.001] and 0.267 [P<0.001] vs 0.539) (see FIG. 2) and 12 to 15 hours post injection (0.475 [P<0.001] and 0.515 [P=0.002] vs 0.753) (see FIG. 3). When compared to the no titration group at 4-6 hours post injection, the incidence of FLS was significantly less for the fast titration group (odds ratio [OR]: 0.179 [0.075, 0.429], P<0.001) and the slow titration group (OR: 0.414 [0.194, 0.994], P=0.023) (see FIG. 4). Similar results were demonstrated at 12-15 hours post injection (fast titration OR: 0.469 [0.272, 0.907], P=0.006; slow titration OR: 0.562 [0.338, 0.936], P=0.027) (see FIG. 4).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for reducing the severity of flu-like symptoms associated with treating a patient having multiple sclerosis with intramuscularly administered interferon-β-1a, comprising:
    providing a kit comprising interferon-β-1a in lyophilized form in a vial, interferon-β-1a in liquid form in a pre-filled syringe, and interferon-β-1a in liquid form in a pre-filled pen;
    administering 7.5 micrograms of interferon-β1a to the patient intramuscularly in week one;
    administering 15 micrograms of interferon-β1a to the patient intramuscularly in week two;
    administering 22.5 micrograms of interferon-β1a to the patient intramuscularly in week three; and
    administering 30 micrograms of interferon-β1a to the patient intramuscularly in week four and each week thereafter,
thereby reducing severity of flu-like symptoms experienced by the patient, wherein the severity of flu-like symptoms experienced by the patient is reduced at 4-6 hours and at 12-15 hours after each intramuscular administration of interferon-β-1a throughout an eight week period which includes once a week intramuscular administration of 30 micrograms of interferon-β-1a to the patient in weeks four through eight when compared to the severity of flu-like symptoms at 4-6 hours and at 12-15 hours after each intramuscular administration of interferon-β-1a to a patient having multiple sclerosis according to:
  (i) a second schedule comprising once a week intramuscular administration of 30 micrograms of interferon-β-1a to the patient having multiple sclerosis for eight weeks; and
  (ii) a third schedule comprising intramuscular administration of 7.5 micrograms of interferon-β-1a to the patient in weeks one and two, intramuscular administration of 15 micrograms of interferon-β-1a to the patient in weeks three and four, intramuscular administration of 22.5 micrograms of interferon-β-1a to the patient in weeks five and six and intramuscular administration of 30 micrograms of interferon-β-1a to the patient in week seven and each week thereafter.

2. The method of claim 1, wherein fever, muscle aches, chills, sweating, fatigue, headache, and/or malaise in said patient are reduced.

3. The method of claim 1, further comprising administration of an analgesic or anti-inflammatory drug, or a mixture thereof.

4. The method of claim 3, wherein the drug is a steroid.

5. The method of claim 3, wherein the drug is a non-steroidal anti-inflammatory agent.

6. The method of claim 3, wherein the drug is acetaminophen.

7. The method of claim 3, wherein the drug is ibuprofen.

8. The method of claim 1, wherein the flu-like symptoms are reduced by at least 40% at 4-6 hours post-injection.

9. The method of claim 1, wherein the flu-like symptoms are reduced by at least 10% at 12-15 hours post-injection.

10. The method of claim 1, further comprising providing a vial adapter.

11. The method of claim 1, wherein the pre-filled pen comprises an auto-injector.

12. The method of claim 1, further comprising a needle stick prevention device.

13. The method of claim 12, wherein the needle-stick prevention device comprises a needle shield.

14. The method of claim 13, wherein the shield is activated manually by the patient.

15. The method of claim 13, wherein the shield is automated.

16. The method of claim 15, wherein the automated shield is activated by the patient.

17. The method of claim 15, wherein the needle is automatically shielded without any action by the patient.

18. The method of claim 15, wherein the needle is shielded without any action by the patient.

19. The method of claim 1, wherein the kit further comprises a dose-limiting titration device.

* * * * *